United States Patent [19]

Umemoto et al.

[11] Patent Number: 5,569,771

[45] Date of Patent: Oct. 29, 1996

[54] (HALOALKYL) DIBENZOONIUMSULFONATE AND ITS PRODUCTION METHODS; AND A HALOALKYLATING AGENT AND HALOALKYLATING METHODS

[75] Inventors: Teruo Umemoto; Sumi Ishihara; Kenji Adachi, all of Tsukuba, Japan

[73] Assignee: Daikin Industries Ltd., Osaka, Japan

[21] Appl. No.: 347,469

[22] PCT Filed: Apr. 6, 1994

[86] PCT No.: PCT/JP94/00582

§ 371 Date: Dec. 13, 1994

§ 102(e) Date: Dec. 13, 1994

[87] PCT Pub. No.: WO94/24122

PCT Pub. Date: Oct. 27, 1994

[30] Foreign Application Priority Data

Apr. 14, 1993 [JP] Japan ................... 5-111099
May 21, 1993 [JP] Japan ................... 5-142648

[51] Int. Cl.[6] ............... C07D 333/76; C07D 345/00
[52] U.S. Cl. ................... 549/44; 549/48; 562/899
[58] Field of Search ................ 549/44, 48; 562/899

[56] References Cited

U.S. PATENT DOCUMENTS 2,527,335 10/1950 Richter et al. .................... 549/44

OTHER PUBLICATIONS

Mar., "Advanced Organic Chemistry", 3rd Ed., 1985. pp. 468–470 & 473–475.

*Primary Examiner*—José G. Dees
*Assistant Examiner*—Mary C. Cebulak
*Attorney, Agent, or Firm*—Armstrong, Westerman, Hattori, McCleland & Naughton

[57] ABSTRACT

(Haloalkyl)dibenzooniumsulfonate represented by the following general formula (I):

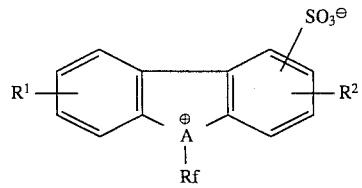

By using this compound as the haloalkylating agent, haloalkylated organic compounds being non-water-soluble as the objective product can very easily be separated in the post-treatment process. This haloalkylating agent can be produced from cheap materials on an industrial basis because those materials for compounding are industrially easily available or can easily be synthesized industrially.

10 Claims, No Drawings

(HALOALKYL) DIBENZOONIUMSULFONATE AND ITS PRODUCTION METHODS; AND A HALOALKYLATING AGENT AND HALOALKYLATING METHODS

This application is a 371 of PCT/JP94/00582 filed Apr. 6, 1994.

FIELDS OF THE INVENTION

The present inventions relate to a new substance named (haloalkyl)dibenzooniumsulfonate and its production methods; and a haloalkylating agent and haloalkylating methods.

PRIOR ART (Haloalkyl)dibenzoonium salts and their substitution compounds are useful known haloalkylating agents for organic compounds [See Tetrahedron Lett., Vol. 31, p3579 (1990); Japanese Patent Opening No.197479/91; and J. Am. Chem. Soc., Vol. 115, p2156 (1993)].

It has, however, turned out that the known (haloalkyl)dibenzoonium salts and their substituted compounds as haloalkylating agents cause difficult problems in the post-treatment process.

For example, haloalkylating the sodium salt of 2-methyl-1, 3-cyclopentanedione with (haloalkyl)dibenzothiophenium trifluoromethanesulfonate simultaneously generate equivalent dibenzothiophene and sodium trifluoromethanesulfonate beside 2-(haloalkyl)-2-methyl-1, 3-cyclopentanedione as shown in the following formula.

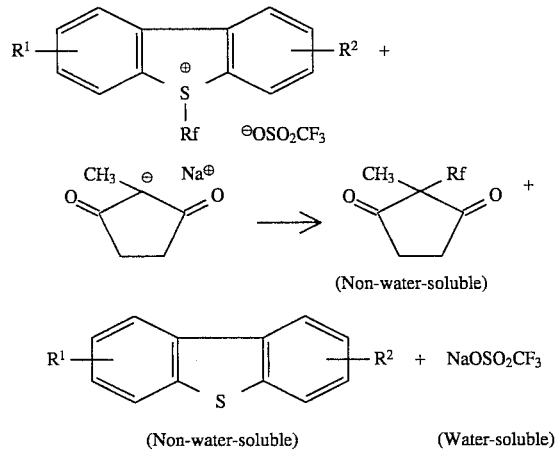

While the latter sodium trifluoromethanesulfonate of the above-stated products can easily be removed from the reaction mixture liquid by rinsing it because that substance is water-soluble, the former dibenzothiophene cannot be separated through the rinsing process from 2-(haloalkyl)-2-methyl-1, 3-cyclopentanedione to be obtained because both substances are non-water-soluble.

As a result, a very complicated process is required to separate the dibenzothiophene from the reaction mixture liquid. This is a serious shortcoming in the prior art for this type of production.

OBJECTS OF THE INVENTIONS

The object of the present inventions is to provide new compounds suitable for industrial production from cheap materials by enabling the simpler separation of those objective products from haloalkylated substances in the post-treatment process.

CONSTITUENTS OF THE INVENTIONS

To solve the above-stated problem, the inventors have thoroughly studied an idea of integrating a water-soluble functional group into a dibenzoheterocycle. As a consequence, they succeeded in introducing (bonding) a water-soluble sulfonic acid anion group to a dibenzoheterocyclic compound. The inventors have thereby attained the object and created the present inventions.

Dibenzoheterocyclic sulfonic acid or its metallic salts which are produced by haloalkylation by means of the invented substance as the haloalkylating agent can easily be separated through the rinsing process because those products are water-soluble. Dibenzoheterocyclic sulfonic acid or its metallic salts can also be separated through the simple filtration process because they are not soluble in conventional organic solvents.

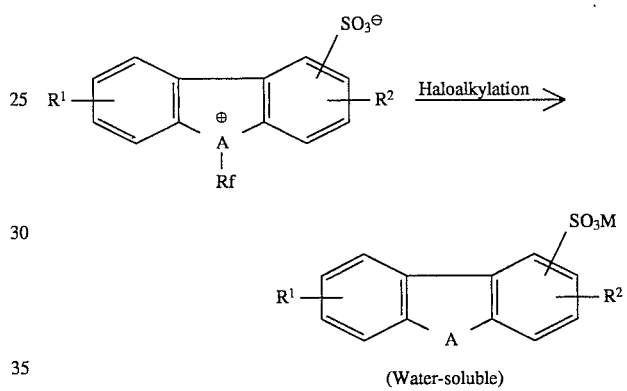

(Water-soluble)

(In the above formula, Rf, A, $R^1$ and $R^2$ are the same as defined in the general formula (I) of the present inventions, and M means a hydrogen atom or a metal atom.)

The present inventions relate to (haloalkyl)dibenzooniumsulfonate as represented by the following general formula (I) that is useful as a good haloalkylating agent.

General formula (I):

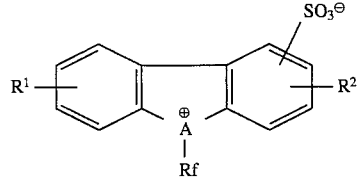

(In the above general formula, Rf means a haloalkyl group with 1 to 10 carbons; A is a sulfur atom, a selenium atom, or a tellurium atom; and $R^1$ and $R^2$ are hydrogen atoms, nitro groups, or lower alkyl groups with 1 to 4 carbons.)

The present inventions also provide effective methods of haloalkylating organic compounds by means of the invented haloalkylating agent.

In the above-stated general formula (I) created by these inventions, specific examples for Rf are normal chain or branching haloalkyl groups with 1 to 10 carbons (preferably fluoroalkyl groups, or particularly preferably perfluoroalkyl groups), such as: $CF_3$, $C_2F_5$, $C_3F_7$, $C_4F_9$, $C_5F_{11}$, $C_6F_{13}$, $C_7F_{15}$, $C_8F_{17}$, $C_9F_{19}$, $C_{10}F_{21}$, $CHF_2$, $C_2HF_4$, $C_3HF_6$, $C_4HF_8$, $C_5HF_{10}$, $C_6HF_{12}$, $C_7HF_{14}$, $C_8HF_{16}$, $C_9HF_{18}$, $C_{10}HF_{20}$, $CH_2F$, $C_2H_2F_3$, $C_3H_2F_5$, $C_4H_2F_7$, $C_5H_2F_9$, $C_6H_2F_{11}$, $C_7H_2F_{13}$, $C_8H_2F_{15}$, $C_9H_2F_{17}$, $C_{10}H_2F_{19}$, $C_2H_3F$, $C_3H_3F_4$, $C_4H_3F_6$, $C_5H_3F_8$, $C_6H_3F_{10}$, $C_7H_3F_{12}$, $C_8H_3F_{14}$, $C_9H_3F_{17}$, $C_{10}H_3F_{18}$, $CClF_2$, $C_2ClF_4$, $C_3ClF_6$, $C_4ClF_8$, $C_5ClF_{10}$, $C_6ClF_{12}$, $C_7ClF_{14}$, $C_8ClF_{16}$, $C_9ClF_{18}$, $C_{10}ClF_{20}$, $CBrF_2$, $C_2BrF_4$, $C_3BrF_6$, $C_4BrF_8$, $C_5BrF_{10}$, $C_6BrF_{12}$, $C_7BrF_{14}$, $C_8BrF_{16}$, $C_9BrF_{18}$, $C_{10}BrF_{20}$, $CF_2I$, $C_2F_4I$, $C_3F_6I$, $C_4F_8I$, $C_5F_{10}I$, $C_6F_{12}I$, $C_7F_{14}I$, $C_8F_{16}I$, $C_9F_{19}I$, and $C_{10}F_{20}I$.

Specific examples of lower alkyl groups for $R^1$ and $R^2$ in the above general formula (I) of the present inventions are normal chain or branching alkyl groups with 1 to 4 carbons such as methyl groups, ethyl groups, propyl groups, and butyl groups.

In the above general formula (I), A, $R^1$ and $R^2$ can be combined as follows:

(1) A is a sulfur atom, and $R^1$ and $R^2$ are hydrogen atoms, nitro groups or alkyl groups with 1 to 4 carbons;

(2) A is a selenium atom, and $R^1$ and $R^2$ are hydrogen atoms; or (3) A is a tellurium atom, and $R^1$ and $R^2$ are hydrogen atoms.

The invented compound shown by the above general formula (I) can be produced in the process represented by the following reaction formula i.

Reaction formula i

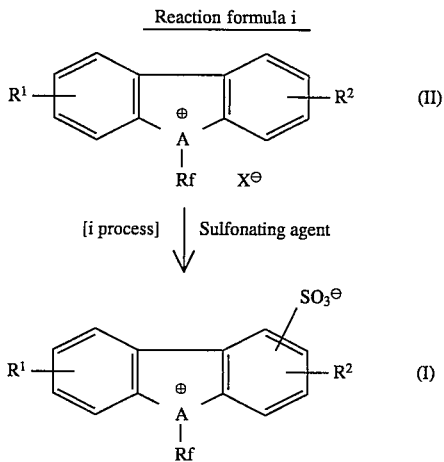

(In the above reaction Formula, Rf, A, $R^1$ and $R^2$ are the same as mentioned above, and $X^\ominus$ is a conjugated base of a Brönsted acid.)

[i process]

This process produces (haloalkyl)dibenzooniumsulfonate represented by the above general Formula (I) by reacting (haloalkyl)dibenzoonium salt represented by the above general Formula (II) with a sulfonating agent.

The compound of the general Formula (II) used in this process is the known compound or the one that can be compounded easily as the known one [See Tetrahedron Lett., Vol. 31, p3579 (1990); Japanese Patent Opening No. 197479/91; Bull. Chem. Soc. Jpn., Vol. 64, p2008 (1991), and J. Am. Chem. Soc., Vol. 115, p2156 (1993)].

Sulfonating agents which can be used in this process include fuming sulfuric acid ($SO_3$—$H_2S_4$), sulfuric acid-trifluoromethanesulfonic anhydride, but fuming sulfuric acid can be preferably used in terms of economy. $SO_3$ concentration of the fuming sulfuric acid is normally 5% to 80%, or preferably 10% to 70%.

The amount of sulfonating agent used in this process can be suitably decided in a range of 0.8 mol to 10 mol, or preferably 1 mol to 5 mol, of effective sulfonating agent molecules ($HSO_3^+$ for 1 mol of the compound represented by the formula (II).

The reaction temperature can be in a range of 0° C. to 100° C. or preferably the room temperature to 80° C.

The reaction of this process is effected by mixing the compound represented by the formula (II) with the above-mentioned sulfonating agent.

In the above general formula (II), X is a conjugated base of a Brönsted acid. Those Brönsted acids include strong acids such as sulfuric acid, monomethyl sulfuric acid, chlorosulfonic acid, fluorosulfonic acid, methanesulfonic acid, trifluoromethanesulfonic acid, difluoromethanesulfonic acid, trichloromethanesulfonic acid, perfluoroethanesulfonic acid, trifluoroethanesulfonic acid, tetrafluoroethanesulfonic acid, butanesulfonic acid, perfluorobutanesulfonic acid, perfluorooctanesulfonic acid, benzensulfonic acid, toluenesulfonic acid, nitrobenzensulfonic acid, trifluoroacetic acid, hydrogen chloride, $HBF_4$, $HSbF_6$, $HSbCl_5F$, $HSbCl_6$, $HAsF_6$, $HBCl_4$, $HBCl_3F$, $HAlCl_4$, $HAlCl_3F$, $HPF_6$, and $HClO_4$.

(Haloalkyl)dibenzooniumsulfonate containing a nitro group as $R^1$ in the above general formula (I) of these inventions can also be produced according to the following reaction formula ii.

Reaction formula ii

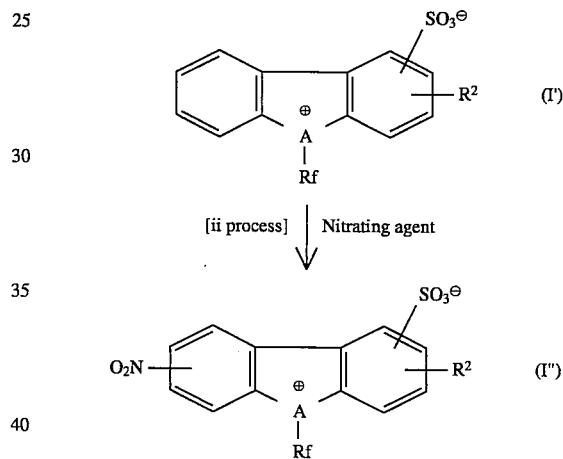

(In this reaction formula, Rf, A and $R^2$ are the same as mentioned in the above.)

[ii process]

This process produces nitro-substituted (haloalkyl)dibenzooniumsulfonate as represented by the above general formula (I") by reacting the compound represented by the above general formula (I') with a nitrating agent.

The compound of the formula (I') used in this process can be produced through the i process of the present inventions.

Nitrating agents that can be used in this process include nitric acid-sulfuric acid, fuming nitric acid-sulfuric acid, nitric acid-fuming sulfuric acid, fuming nitric acid-fuming sulfuric acid, nitric acid-trifluoromethanesulfonic acid, nitric acid-trifluoromethanesulfonic anhydride, nitric acid-chlorosulfonic acid, nitric acid-fluorosulfonic acid, nitronium trifluoromethanesulfonate, nitronium tetrafluoroborate, nitronium hexafluorophosphate, nitronium hexafluoroantimonate, nitironium hexafluoroarsenate.

The amount of the nitrating agent used for this can be suitably decided in a range of 0.8 mol to 10 mol, or preferably 1 mol to 5 mol, of effective nitrating agent molecules ($NO_2^+$) for 1 mol of the compound represented by the formula (I').

The reaction temperature can be in a range of 0° C. to 100° C., or preferably the room temperature to 80° C.

In this process, the nitrating agent, if a liquid one is used, can also be used as the reaction solvent. On the other hand, if a solid nitrating agent is used, a reaction solvent can be used preferably. Substances that can be used as the reaction solvent include sulfuric acid, trifluoromethanesulfonic acid, nitromethane, methylene chloride, chloroform, and carbon tetrachloride.

In the above reaction formulas (i) and (ii), A, $R^1$ and $R^2$ can be combined as follows:

(1) A is a sulfur atom, and $R^1$ and $R^2$ are hydrogen atoms, nitro groups or alkyl groups with 1 to 4 carbons;

(2) A is a selenium atom, and $R^1$ and $R^2$ are hydrogen atoms; or (3) A is a tellurium atom, and $R^1$ and $R^2$ are hydrogen atoms.

INDUSTRIAL APPLICABILITY OF THE INVENTION (Haloalkyl)dibenzooniumsulfonate represented by the above general formula (I) of the present inventions is produced by introducing (bonding) a water-soluble sulfonic acid anion group to a dibenzoheterocycle. Therefore, dibenzoheterocyclic sulfonic acid or its metallic salts that are produced in a process using (haloalkyl)dibenzooniumsulfonate as the haloalkylating agent can easily be separated through the rinsing process because those products are water-soluble. Dibenzoheterocyclic sulfonic acid or its metallic salts can also be separated through the simple filtration process because they are not soluble in conventional organic solvents. Haloalkylated organic compounds (non-water-soluble) as the objective product can very easily be separated in the post-treatment process.

The compounds as raw materials represented by the above general formulas (II) and (I') are industrially available or can easily be synthesized. Accordingly the compound represented by the above general formula (I) can be produced with cheap materials in an industrial sense.

EMBODIMENTS

Further details of the present inventions are provided through their embodiments below. The inventions shall, however, never be construed as restricted by these embodiments in any sense.

Embodiment 1

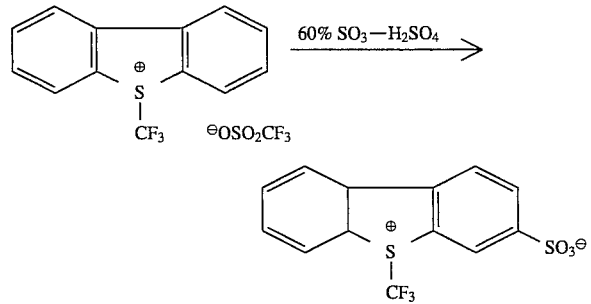

After 5.5 ml of 60% fuming sulfuric acid was cooled in the ice bath, it was added with 7.90 g (19.7 mmol) of S-(trifluoromethyl)dibenzothiophenium trifluoromethanesulfonate. When the exothermic reaction was completed, the ice bath was removed and then the mixture was stirred for 5.5 hours at the room temperature.

After the stirring, the mixture was added with ether and a small amount of methanol while it was cooled in the ice bath. When the exothermic reaction was completed, the ice bath was removed, and then the upper layer of ether was taken away but the lower oily layer left in the container.

The left oily layer was well washed with a large amount of ether and then added with acetone to make crystals deposit. The deposited crystals were separated with a filter. 4.76 g (73% yield) of S-(trifluoromethyl)dibenzothiophenium-3-sulfonate was obtained by drying the crystals. A sample for elementary analysis was produced through recrystalization with methanol.

Analysis data of this product were as follows:

Melting point: 160° C. to 165° C. (accompanied by decomposition)

$^1$H-NMR (ppm, in heavy methanol): 7.91 (1H, t. d., J=8, 1 Hz, 7-H) 8.10 (1H, t. d., J=8, 1 Hz, 8-H) 8.41 (1H, d. d., J=8, 1 Hz, 2-H) 8.48 (1H, d. d., J=8, 1 Hz, 9-H) 8.49 (1H, d, J=8 Hz, 1H) 8.53 (1H, d, J=8 Hz, 6-H) 8.88 (1H, d, J=1 Hz, 4-H)

$^{19}$F-NMR (ppm, in heavy methanol, $CFCl_3$ internal standard): 53.9 (s)

Mass (m/e) (FAB method): 333 ($M^+$+1) 264 ($M^+$+1−$CF_3$)

IR(KBr): 3510, 3465, 3096, 1652, 1456, 1235, 1117, 1077, 1035, 665, 617 $cm^{-1}$

Elementary analysis: Measured value: C, 44.19; H, 2.57%
Calculated value ($C_{13}H_7F_3O_3S_2 \cdot H_2O$): C, 44.57; H, 2.59%

Embodiment 2

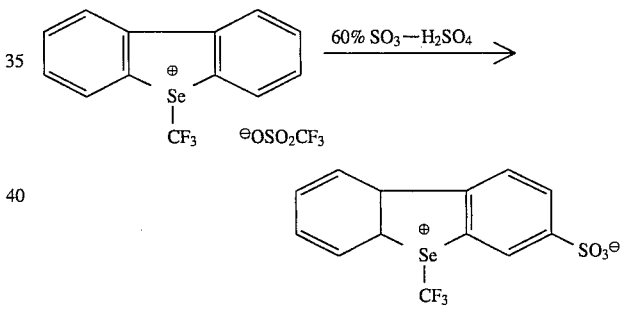

0.56 ml of 60% fuming sulfuric acid was added with 0.898 g (2 mmol) of Se-(trifluoromethyl)dibenzoselenophenium triuoromethanesulfonate. The reaction container was placed in an oil bath of 40° C. temperature, and the mixture was stirred for 2 hours.

After the heat was radiated out, the mixture was added with a small amount of ether, and then with a small amount of methanol while it was cooled in the dry ice-acetone bath. After the bath was removed, the mixture was added with ether while the mixture temperature was raised up to the room temperature. The reaction liquid separated into two layers. The upper layer of ether was taken away but the lower oily layer left in the container.

The left oily layer was well washed with a large amount of ether and then added with acetone to make crystals deposit. The deposited crystals were separated with a filter. 0.548 g (72% yield) of Se-(trifluoromethyl)dibenzoselenophenium-3-sulfonate was obtained by drying the crystals. A sample for elementary analysis was produced through recrystalization with methanol.

Analysis data of this product were as follows:

Melting point: 175° C. to 178° C. (accompanied by decomposition)

$^1$H-NMR (ppm, in heavy dimethylsulfoxide): 7.77 (1H, t. d., J=8, 1 Hz, 7-H) 7.92 (1H, t. d., J=8, 1 Hz, 8-H) 8.07 (1H, d. d., J=8, 1 Hz, 2-H) 8.36 (1H, d., J=8 Hz, 1-H) 8.38 (1H, d. d., J=8, 1 Hz, 6-H) 8.47 (1H, d. d., J=8, 1 Hz, 9-H) 8.78 (1H, d. J=1 Hz, 4-H)

$^{19}$F-NMR (ppm, in heavy dimethylsulfoxide, CFCl$_3$ internal standard): 46.5 (s)

Mass (m/e) (FAB method): 383, 381, 379, 378, 377 (M$^+$+1), 314, 312, 310, 309, 308 (M$^+$+1–CF$_3$)

IR(KBr): 3864, 1183, 1117, 1076, 1028, 773, 743, 705, 656, 615 cm$^{-1}$

Elementary analysis: Measured value: C, 38.90; H, 2.14% Calculated value (C$_{13}$H$_7$F$_3$O$_3$SSe.H$_2$O): C, 39.31; H, 2.28%

Embodiment 3

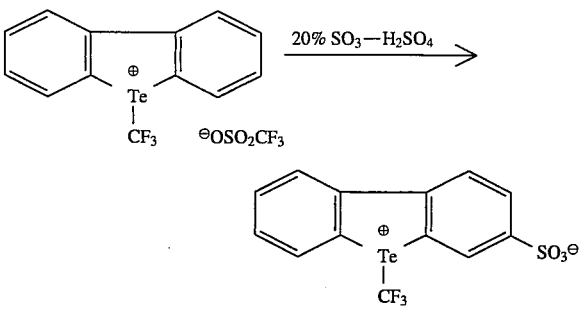

0.272 ml of 20% fuming sulfuric acid was added with 0.498 g (1 mmol) of Te-(trifluoromethyl)dibenzotellurophenium trifluoromethanesulfonate. The container was left at the room temperature for 10 minutes, and then the mixture was stirred for 1 hours while the container was placed in the oil bath at 40° C.

After the heat was radiated out, the mixture was added with a small amount of ether, and then with a small amount of methanol while it was dipped in the dry ice-acetone bath. After the bath was removed, the mixture was added with ether while the mixture temperature was raised up to the room temperature. Then white crystals were deposited.

After some time of still standing, the upper layer was taken away. The left liquid was added with a small amount of methanol and a large amount of ether to wash the crystals. The deposited crystals were separated with a filter, and then well washed with acetone and ether. 0.394 g (92% yield) of Te-(trifluoromethyl)dibenzotellurophenium-3-sulfonate was obtained by drying the crystals.

Analysis data of this product were as follows:

Melting point: 271° C. to 275° C.

$^1$H-NMR (ppm, in heavy dimethylsufoxide): 7.67 (1H, t. d., J=8, 1 Hz, 7-H) 7.80 (1H, t. d., J=8, 1 Hz, 8-H) 7.95 (1H, d. d., J=8, 1.6 Hz, 2-H) 8.23 (1H, d. d., J=8, 1 Hz, 9-H) 8.26 (1H, d, J=8 Hz, 1-H) 8.28 (1H, d, J=8 Hz, 6-H) 8.53 d, J=1.6 Hz, 4-H)

$^{19}$F-NMR (ppm, in heavy dimethylsulfoxide, CFCl$_3$ internal standard): 43.6 (s)

Mass (m/e) (FAB method): 431, 429, 427, 426 (M$^+$+1), 362, 360, 358, 357, 356 (M$^+$+1–CF$_3$)

IR(KBr): 3422, 1152, 1120, 1078, 1022, 774, 730, 702, 653, 616 cm$^{-1}$

Elementary analysis: Measured value: C, 34.00; H, 2.05% Calculated value (C$_{13}$H$_7$F$_3$O$_3$STe.½H$_2$O): C, 34.33; H, 2.22%

Embodiment 4

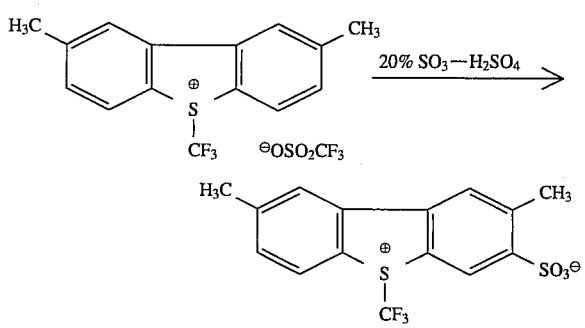

0.262 ml of 20% fuming sulfuric acid was added with 0.215 g (0.5 mmol) of S-(trifluoromethyl)-2, 8-dimethylbenzothiophenium trifluoromethanesulfonate. The container was left at the room temperature for 10 minutes and then placed in an oil bath of 40° C. temperature while the mixture was stirred for 1 hour.

After the heat was radiated out, the mixture was added with a small amount of ether and then with a small amount of methanol while the container was placed in the dry ice-acetone bath. After the bath was removed, the mixture was added with ether while the mixture temperature was raised up to the room temperature. The liquid separated into two layers. The upper layer of ether was taken away but the lower oily layer left in the container.

The left oily layer was well washed with a small amount of methanol and a large amount of ether to make crystals deposit. The deposited crystals were separated with a filter and well washed with ether. 0.151 g (80% yield) of S-(trifluoromethyl)-2, 8-dimethyldibenzothiophenium-3-sulfonate was obtained by drying the crystals. A sample for elementary analysis was produced through recrystalization with methanol-ether.

Analysis data of this product were as follows:

Melting point: 188° C. to 190° C. (accompanied by decomposition)

$^1$H-NMR (ppm, in heavy dimethylsufoxide): 2.56 (3H, s, 8-CH$_3$), 2.77 (3H, s, 2-CH$_3$) 7.67 (1H, d. d., J=8, 1 Hz, 7-H) 8.30 (1H, s, 1-H) 8.32 (1H, s, 9-H) 8.51 (1H, d, J=8 Hz, 6-H) 8.95 (1H, s, 4-H)

$^{19}$F-NMR (ppm, in heavy dimethylsulfoxide, CFCl$_3$ internal standard): 53.7 (s)

Mass (m/e) (FAB method): 361 (M$^+$+1),

IR(KBr): 3450, 1207, 1103, 1068, 1035, 712, 626 cm$^{-1}$

Elementary analysis: Measured value: C, 49.08; H, 3.10% Calculated value (C$_{15}$H$_{11}$F$_3$O$_3$S$_2$ ½H$_2$O): C, 48.78; H, 3.27%

Embodiment 5

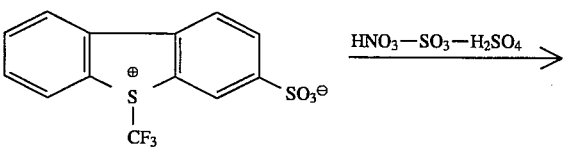

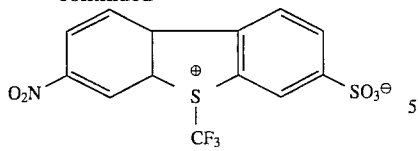

A mixture of 1.0 ml of 20% fuming sulfuric acid and 0.3 ml of concentrated nitric acid was added with S-(trifluoromethyl)dibenzothiophenium-3-sulfonate little by little at the room temperature.

The mixture was stirred for 16 hours at the room temperature, and then added with ether little by little while the container was cooled with ice. After the exothermic reaction completed, the ether layer was removed from the liquid, and then ether was added to the liquid to wash the deposit. Then the ether was taken away.

After the deposit was well stirred with a small amount of methanol added, it was added with ether and then filtered to obtain the crystals deposited. The obtained crystals were washed with a mixture of methylene chloride-methanol (10/1). Finally, 852 mg (75% yield) of S-(trifluoromethyl)-7-nitrodibenzothiophenium-3-sulfonate was obtained by drying the crystals under a reduced pressure. A sample for elementary analysis was produced through recrystalization with dimethylsulfoxide-water-acetonitrile.

Analysis data of this product were as follows:

Melting point: 196° C. to 210° C.

$^1$H-NMR (ppm, in heavy dimethylsufoxide): 9.64 (1H, d, J=2.1Hz, 6-H) 9.05 (1H, d, J=1.2 Hz, 4-H) 8.86 (1H, d. d., J=2.1, 8.6 Hz, 8-H) 8.75 (1H, d, J=8.6 Hz, 9-H) 8.65 (1H, d, J=8.1 Hz, 1-H) 8.27 (1H, d. d., J=1.2, 8.1 Hz, 2-H)

$^{19}$F-NMR (ppm, in heavy dimethylsulfoxide, CFCl$_3$ internal standard): 50.9 (s)

Mass (m/e) (FAB method): 378 (M$^+$+1), 307 (M$^+$–1–CF$_3$)

IR(KBr): 3460, 3097, 1599, 1534, 1351, 1228, 1114, 1076, 1034, 809, 757, 670, 633 cm$^{-1}$

Elementary analysis: Measured value: C, 39.25; H, 2.11: N 3.44% Calculated value (C$_{13}$H$_6$F$_3$NO$_5$S$_2$.H$_2$O): C, 39.50; H, 2.04; N 3.54%

Embodiment 6

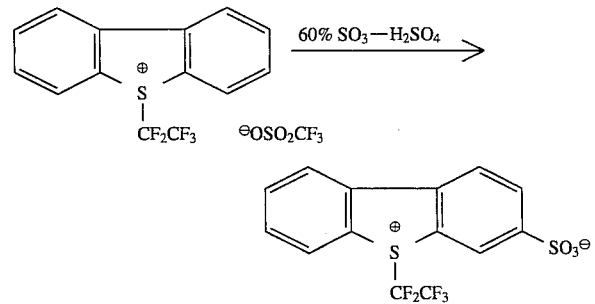

0.28 ml of 60% fuming sulfuric acid was added with 452 mg (1 mmol) of S-(perfluoroethyl)dibenzothiophenium trifluoromethanesulfonate. Then the mixture was stirred at 40° C. for 6 hours.

After the reaction, the mixture was added with ether and then with a small amount of methanol while it was cooled in the dry ice-acetone bath. Then, the mixture was added with ether while the mixture temperature was raised up to the room temperature. The reaction liquid separated into two layers. The upper layer was taken away. The lower oily layer left was washed with a large amount of ether.

The obtained viscous oily substance was dissolved in a small amount of methanol, and then added with ether to make crystals deposit. 0.33 g (86% yield) of S-(perfluoroethyl)dibenzothiophenium- 3-sulfonate was obtained by filtering the deposited crystals. 0.26 g (69% yield) of this product for elementary analysis sample was produced through recrystalization with methanol-ether.

Analysis data of this product were as follows:

Melting point: 174° C. to 178° C. (accompanied by decomposition)

$^1$H-NMR (ppm, in heavy dimethylsufoxide): 7.87 (1H, t. d., J=8, 1 Hz, 7-H) 8.07 (1H, t. d., J=8, 1 Hz, 8-H) 8.22 (1H, d. d., J=8, 1 Hz, 2-H) 8.51 (1H, d, J=8 Hz, 1-H) 8.53 (1H, d. d., J=8, 1 Hz, 6-H) 8.63 (1H, d, J=8 Hz, 9-H) 8.91 (1H, s, 4-H)

$^{19}$F-NMR (ppm, in heavy dimethylsulfoxide, CFCl$_3$ internal standard): 76.6 (3F, s, CF$_3$), 97.8 (1F, d. m., J=201 Hz, SCF) 98.5 (1F, d. m., J=201 Hz, SCF)

Mass (m/e) (FAB method): 383 (M$^+$+1), 264 (M$^+$+1—C$_2$F$_5$)

IR(KBr): 3093, 1330, 1244, 1214, 1195, 1113, 1032, 932, 750, 662, 611, 520 cm$^{-1}$

Elementary analysis: Measured value: C, 43.82; H, 1.72% Calculated value (C$_{14}$H$_7$F$_5$O$_3$S$_2$): C, 43.98; H, 1.85%

Embodiment 7

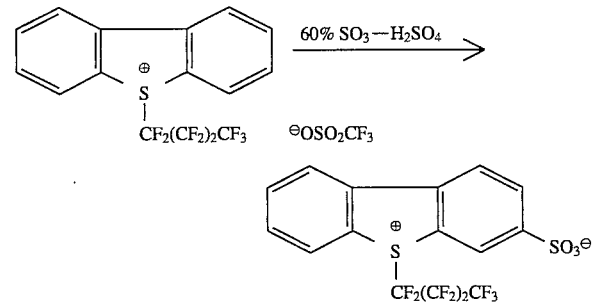

0.65 g (67% yield) of S-(perfluoro-n-butyl) dibenzothiophenium-3-sulfonate was obtained by the same process and post-treatment process as the embodiment 6 except that 1.10 g (2 mmol) of S-(perfluoro-n-butyl)dibenzothiophenium trifluoromethanesulfonate instead of S-(perfluoroethyl)dibenzothiophenium trifluoromethanesulfonate, and 0.56 ml of 60% fuming sulfuric acid were used.

Analysis data of this product were as follows:

Melting point: 190° C. to 198° C. (accompanied by decomposition)

$^1$H-NMR (ppm, in heavy dimethylsufoxide): 7.87 (1H, t, J=8 Hz, 7-H) 8.07 (1H, t, J=8 Hz, 8-H) 8.23 (1H, d. d., J=8, 1 Hz, 2-H) 8.51 (1H, d, J=8 Hz, 1-H) 8.53 (1H, d, J=8 Hz, 6-H) 8.62 (1H, d, J=8 HZ, 9-H) 8.88 (1H, s, 4-H)

$^{19}$F-NMR (ppm, in heavy dimethylsulfoxide, CFCl$_3$ internal standard): 79.6 (3F, t, J=9 Hz, CF$_3$), 93.3 (1F, d. t., J=200, 13 Hz, SCF) 94.5 (1F, d. t., J=200, 13 Hz, SCF) 116.4 (2F, m, CF$_2$) 125.1 (2F, m, CF$_2$)

Mass (m/e) (FAB method): 483 (M$^+$1), 264 (M$^+$+1–C$_4$F$_9$)

IR(KBr): 3091, 1349, 1230, 1205, 1112, 1029, 725, 695, 661, 616, 518 cm$^{-1}$

Elementary analysis: Measured value: C, 39.77; H, 1.41%
Calculated value ($C_{16}H_7F_9O_3S_2$): C, 39.84; H, 1.46%

Embodiment 8

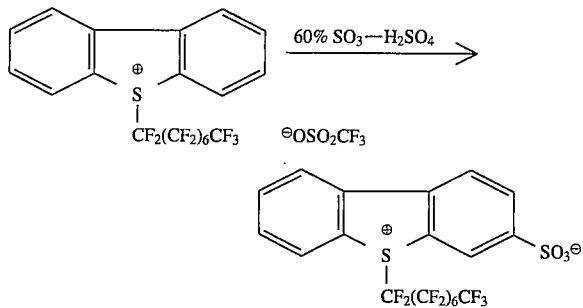

0.84 ml of 60% fuming sulfuric acid was added with 2.26 g (3 mmol) of S-(perfluoro-n-octyl)dibenzothiophenium trifluoromethanesulfonate. The mixture was stirred for 4.5 hours while the container was placed in the bath at a 40° C. temperature, and then stirred for 12 hours at the room temperature.

The mixture was added with ether while it was cooled in the ice bath. Half-solid substance was produced by adding ether to the mixture. Then, the substance was well washed with ether. Then the mixture was added with methanol to make the substance deposit into crystals. The deposited crystals were obtained by filtering. The obtained crystals were washed with ether and methanol, and then dried by a vacuum pump. Finally, 1.75 g (85% yield) of S-(perfluoro-n-octyl)dibenzothiophenium-3-sulfonate was obtained.

Analysis data of this product were as follows:

Melting point: 150° C. to 180° C.

$^1$H-NMR (ppm, in heavy dimethylsufoxide): 7.87 (1H, t. J=8 Hz, 7-H) 8.07 (1H, t. J=8 Hz, 8-H) 8.22 (1H, d. d., J=8, 1 Hz, 2-H) 8.51 (1H, d, J=8 Hz, 1-H) 8.53 (1H, d, J=8 Hz, 6-H) 8.62 (1H, d, J=8 Hz, 9-H) 8.88 (1H, s, 4-H)

$^{19}$F-NMR (ppm, in heavy dimethylsulfoxide, $CFCl_3$ internal standard): 79.7 (3F, t. J=9 Hz, $CF_3$) 93.0 (1F, d. J=200 Hz, SCF) 94.3 (1F, d. J=200, SCF) 115.3 (2F, m, $CF_2$) 120.8 (4F, m, $CF_2×2$) 121.1 (2F, m, $CF_2$) 121.9 (2F, m, $CF_2$) 125.2 (2F, m, $CF_2$)

Mass (m/e) (FAB method): 683 ($M^++1$), 264 ($M^++1-C_8F_{17}$)

IR(KBr): 3428, 3090, 1208, 1152, 1031, 661, 616 cm$^{-1}$

Elementary analysis: Measured value: C, 34.29; H, 1.02%
Calculated value ($C_{20}H_7F_{17}O_3S_2.H_2O$): C, 34.30; H, 1.30%

Embodiment 9

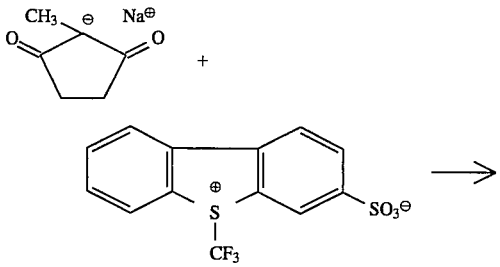

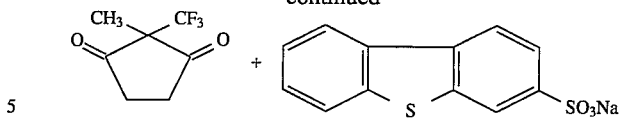

A solution of the sodium salt of 2-methyl-1, 3-cyclopentanedione was prepared by reacting 2.6 mmol of 2-methyl-1, 3-cyclopentanedione with 2.6 mmol of sodium hydride in 5 ml of dimethylformamide as the solvent under the ice cooling condition in an argon atmosphere.

After the reaction liquid was cooled down to −45° C., it was added with 664 mg (2 mmol) of S-(trifluoromethyl)dibenzothiophenium- 3-sulfonate while it was stirred.

Then, the liquid temperature was raised up to the room temperature over a period of about 1 hour, and then the liquid was stirred at the room temperature for 1 hour.

Then, the reaction liquid was added with 2 mmol of benzotrifluoride as the standard substance. A quantitative analysis of the liquid through $^{19}$F-NMR showed that the objective 2-(trifluoromethyl)-2-methyl-1, 3-cyclopentanedione had been produced at a 86% yield.

In the post-treatment process, the reaction liquid was added with water and ether, and filtered with a cellite. The filtered liquid was extracted with ether. The obtained extract was washed with water and then with saturated sodium chloride water, and then dried with anhydrous magnesium sulfate.

After the desiccating agent was filtered out from the extract and the solvent was distilled out, the oily product was obtained. The product did not include sodium dibenzothiophene-3-sulfonate, which was produced together in this reaction.

Analysis data of this oily product were shown below. They are consistent with those for the standard sample of 2-(trifluoromethyl)-2-methyl-1, 3-cyclopentanedione.

$^{19}$F-NMR (in $CDCl_3$, $CFCl_3$ internal standard): 69.8 ppm (s)

$^1$H-NMR (in $CDCl_3$): 1.38 (3H, s, $CH_3$) 2.68 to 3.15 ppm (4H, m, $CH_2$ $CH_2$)

IR(neat): 1740 (CO) cm$^{-1}$

Mass (m/e): 180 ($M^+$), 124, 111, 69 ($CF_3^+$)

Embodiment 10

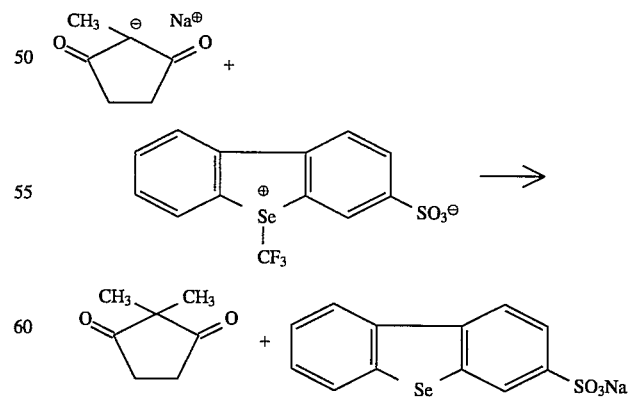

A solution of the sodium salt of 2-methyl-1, 3-cyclopentanedione was prepared by reacting 1.3 mmol of 2-methyl-1, 3-cyclopentanedione with 1.3 mmol of sodium hydride in 4 ml of dimethylformamide as the solvent under the ice cooling condition in an argon atmosphere.

After the reaction liquid was cooled down to −45° C., it was added with 332 mg (1 mmol) of Se-(trifluoromethyl)dibenzoselenophenium-3-sulfonate while it was stirred.

Then, the liquid temperature was raised up to the room temperature over a period of about 1 hour, and then the liquid was stirred at the room temperature for 2.5 hours.

Then, the reaction liquid was added with 1 mmol of benzotrifluoride as the standard substance. A quantitative analysis of the liquid through F-NMR showed that the objective 2-(trifluoromethyl)-2-methyl-1, 3cyclopentanedione had been produced at a 71% yield.

In the post-treatment process, the reaction liquid was added with water and ether, and filtered through a cellite. The filtered liquid was extracted with ether. The obtained extract was washed with water and then with saturated sodium chloride water, and then dried with anhydrous magnesium sulfate.

After the desiccating agent was filtered out from the extract and the solvent was distilled out, the oily product was obtained. The product did not include sodium dibenzoselenophene-3-sulfonate, which was produced together in this reaction.

Analysis data of this oily product were the same as obtained in the embodiment 9.

Embodiment 11

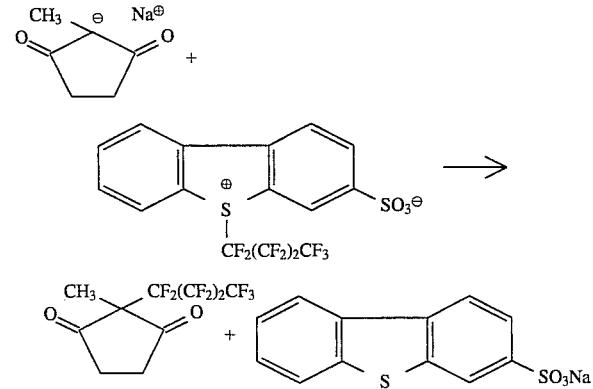

A solution of the sodium salt of 2-methyl-1, 3-cyclopentanedione was prepared by reacting 1.04 mmol of 2-methyl-1, 3-cyclopentanedione with 1.04 mmol of sodium hydride in 3.2 ml of dimethylformamide as the solvent under the ice cooling condition in an argon atmosphere.

After the reaction liquid was cooled down to −45° C., it was added with 386 mg (0.8 mmol) of S-(perfluoro-n-butyl)dibenzothiophenium-3-sulfonate while it was stirred.

Then, the liquid temperature was raised up to the room temperature over a period of about 45 minutes, and then the liquid was stirred at the room temperature for 2.5 hours.

Then, the reaction liquid was added with 0.8 mmol of benzotrifluoride as the standard substance. A quantitative analysis of the liquid through $^{19}$F-NMR showed that the objective 2-(perfluoro-n-butyl)-2-methyl-1, 3-cyclopentanedione had been produced at a 77% yield.

In the post-treatment process, the reaction liquid was added with water and ether, and filtered through a cellite. The filtered liquid was extracted with ether. The obtained extract was washed with water and then with saturated sodium chloride water, and then dried with anhydrous magnesium sulfate.

After the desiccating agent was filtered out from the extract and the solvent was distilled out, the oily product was obtained. The product did not include sodium dibenzothiophene-3-sulfonate, which was produced together in this reaction.

Analysis data of this oily product were shown below. A sample for elementary analysis were produced through the refining process by means of silica gel column chromatography.

$^{19}$F-NMR (ppm, in CDCl$_3$, CFCl$_3$ internal standard): 81.4 (3F, m, CF$_3$) 113.0 (2F, m, CF$_2$) 118.4 (2F, m, CF$_2$) 126.5 (2F, m, CF$_2$)

1H-NMR (ppm, in CDCl$_3$): 1.46 (3H, s, CH$_3$) 2.77 to 3.06 (4H, m, CH$_2$×2)

IR(neat): 1741 (CO) cm$^{-1}$

GC-Mass (m/e): 330 (M$^+$)

Elementary analysis: Measured value: C, 36.44; H, 1.96% Calculated value (C$_{10}$H$_7$F$_9$O$_2$): C, 36.38; H, 2.14%

We claim:

1. (Haloalkyl)dibenzooniumsulfonate represented by the following general formula (I):

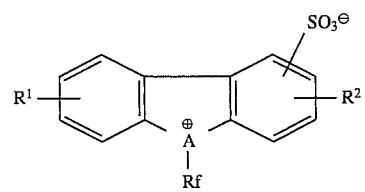

wherein Rf is a haloalkyl group with 1 to 10 carbons; A is a sulfur atom, a selenium atom or a tellurium atom; R$^1$ and R$^2$ are hydrogen atoms, nitro groups or lower alkyl groups with 1 to 4 carbons.

2. The (Haloalkyl)dibenzooniumsulfonate as defined in claim 1 wherein Rf is a straight chain or branching fluoroalkyl group.

3. The (Haloalkyl)dibenzooniumsulfonate as defined in claim 1 or 2 wherein Rf is a straight chain or branching perfluoroalkyl group.

4. The (Haloalkyl)dibenzooniumsulfonate as defined in claim 1 or 2 wherein A is a sulfur atom.

5. The (Haloalkyl) dibenzooniumsulfonate as defined in claim 1 or 2 wherein A is a selenium atom, and R$^1$ and R$^2$ are hydrogen atoms.

6. The (Haloalkyl)dibenzooniumsulfonate as defined in claim 1 or 2 wherein A is a tellurium atom, and R$^1$ and R$^2$ are hydrogen atoms.

7. (Haloalkyl)dibenzooniumsulfonate as defined in claim 3 wherein A is a sulfur atom, and R$^1$ and R$^2$ are hydrogen atoms, nitro groups or alkyl groups with 1 to 4 carbons.

8. (Haloalkyl)dibenzooniumsulfonate as defined in claim 3 wherein A is a selenium atom, and R$^1$ and R$^2$ are hydrogen atoms.

9. (Haloalkyl)dibenzooniumsulfonate as defined in claim 3 wherein A is a tellurium atom, and R$^1$ and R$^1$ are hydrogen atoms.

10. A method of preparing haloalkylated organic compounds by reacting the (haloalkyl)dibenzooniumsulfonate, as defined in one of claims 1, 2, 3, 4, 5, or 6 with the compound to be haloalkylated.

* * * * *